（12) United States Patent
Boday et al.

(10) Patent No.: US 8,323,980 B2
(45) Date of Patent: Dec. 4, 2012

(54) EARLY WARNING SULFUR DETECTION BASED ON CHANGE IN FLUORESCENCE INTENSITY OF POLYMER-BOUND PHOSPHINE COMPOUND

(75) Inventors: Dylan Joseph Boday, Tucson, AZ (US); Joseph Kuczynski, Rochester, MN (US); Robert Ernst Meyer, III, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/463,358

(22) Filed: May 3, 2012

(65) Prior Publication Data

US 2012/0214247 A1  Aug. 23, 2012

Related U.S. Application Data

(62) Division of application No. 12/748,796, filed on Mar. 29, 2010.

(51) Int. Cl.
  *G01N 21/64* (2006.01)
  *G01N 1/22* (2006.01)
  *G01N 1/24* (2006.01)

(52) U.S. Cl. .................... 436/123; 426/172; 426/181

(58) Field of Classification Search ................ None
See application file for complete search history.

(56) References Cited

U.S. PATENT DOCUMENTS

| | | | |
|---|---|---|---|
| 4,677,078 A * | 6/1987 | Minten et al. ............... | 436/136 |
| 5,010,022 A * | 4/1991 | Lindstrom ............... | 436/123 |
| 5,018,856 A | 5/1991 | Harnly et al. | |
| 5,468,372 A | 11/1995 | Seamans et al. | |
| 5,598,451 A | 1/1997 | Ohno et al. | |
| 5,688,736 A | 11/1997 | Seamans et al. | |
| 5,922,943 A | 7/1999 | Chapman, IV | |
| 6,144,455 A | 11/2000 | Tuunanen et al. | |
| 6,372,184 B1 | 4/2002 | LaMoy et al. | |
| 6,746,630 B2 * | 6/2004 | Rooney ................... | 252/600 |
| 6,972,249 B2 | 12/2005 | Akram et al. | |
| 7,036,800 B2 | 5/2006 | Ellis | |
| 7,241,381 B2 | 7/2007 | Warner et al. | |
| 7,671,986 B2 | 3/2010 | Yao | |

(Continued)

OTHER PUBLICATIONS

L.-J. Zhao et al., "Optimization of polystyrene-supported triphenylphosphine catalysts for aza-Morita-Baylis-Hillman reactions", Tetrahedron 61, pp. 12026-12032, 2005, Copyright 2005 Elsevier Ltd.

(Continued)

*Primary Examiner* — Yelena G Gakh
*Assistant Examiner* — Michelle Adams
(74) *Attorney, Agent, or Firm* — Matthew J. Bussan

(57) ABSTRACT

An early warning sulfur detection system for detecting the presence of corrosive gases, especially elemental sulfur ($S_8$), in air employs a substrate that includes a polymer-bound phosphine compound having sulfur-getting functionality. The phosphine compound in the polymer reacts with any airborne elemental sulfur. This reaction is accompanied by a decrease in the fluorescence intensity ($I_f$) of the substrate. The $I_f$ of the substrate is monitored in real time by a spectrofluorometer to detect a change in fluorescence intensity ($\Delta I_f$). In an embodiment sited in a data center, an alarm is triggered if the $\Delta I_f$ is above a predetermined threshold, thereby providing a real-time, early warning to IT professionals that corrective action is required to protect metal conductors from corrosion. Preferably, the phosphine compound in the polymer does not react with other components in the air (e.g., carbon dioxide).

12 Claims, 5 Drawing Sheets

U.S. PATENT DOCUMENTS

2004/0233423 A1  11/2004  Nakayama et al.
2004/0258571 A1  12/2004  Lee et al.
2009/0084157 A1  4/2009  Krogh et al.
2011/0189381 A1  8/2011  Boday et al.

OTHER PUBLICATIONS

Manuel Sebastian et al., "Phosphole-Modified Poly(thiophene)s: Unique Postfunctionalizable Conjugated Polymers That Sense Elemental Chalcogenides", Angew. Chem. Int. Ed., 45, pp. 6152-6155, 2006, Copyright 2006 Wiley-VCH Verlag GmbH & Co., KGaA, Weinheim.

"USB2000-FLG Spectrofluorometer", 2 pages, no date, Copyright 2010 Ocean Optics, Inc. Retrieved from http://www.oceanoptics.comlproducts/usb2000flg.asp.

Koga, Y. et al. "New Preparative Procedure for Photoluminescent Metallopolymers Having a Biphenyl-2,2'-diyl Iridium (III) Unit Bound to a Phosphine Copolymer Ligand," Journal of Polymer Science: Part A: Polymer Chemistry, vol. 44, 4204-4213 (2006).

Naka, N. et al. "Synthesis of Poly(vinylene-phosphine)s: Ring-Collapsed Radical Alternating Copolymerization of Methyl-Substituted Cyclooligophosphine with Acetylenic Compounds," Macromolecules 2007, 40, 4854-4858.

Schindlbauer, H. et al. "Ultraviolet spectra of certain phosphines and phosphine oxides containing benzene, anthracene, and napthalene rings," Monatshefte fuer Chemie, vol. 96, 285-299, (1965); SciFinder CAPLUS English Abstract.

"FluoroMax(R)-4; How to Select a Spectrofluorometer," HORIBA Jobin Yvon, 2006, pp. 1-8.

* cited by examiner

EARLY WARNING SULFUR DETECTION BASED ON CHANGE IN FLUORESCENCE INTENSITY OF POLYMER-BOUND PHOSPHINE COMPOUND

CROSS-REFERENCE TO RELATED APPLICATION

This patent application is a divisional application of pending U.S. patent application Ser. No. 12/748,796, filed Mar. 29, 2010, entitled "EARLY WARNING SULFUR DETECTION BASED ON CHANGE IN FLUORESCENCE INTENSITY OF POLYMER-BOUND PHOSPHINE COMPOUND", which is hereby incorporated herein by reference in its entirety.

BACKGROUND OF THE INVENTION

1. Field of Invention

The present invention relates in general to the field of corrosion protection for metal conductors used in electronic devices. More particularly, the present invention relates to real-time, early warning detection of corrosive gases, especially elemental sulfur ($S_8$), in air based on a change in the fluorescence intensity of a substrate that includes a polymer-bound phosphine compound having sulfur-getting functionality.

2. Background Art

Acid-bearing gases in air (e.g., the air within a data center) can lead to a greater incidence of corrosion-induced hardware failures in computer systems and other electronic devices. This problem is especially prone to occur in industrialized countries. Sulfur components (e.g., elemental sulfur, hydrogen sulfide, and/or sulfur oxides) in the air are particularly troublesome gases. It has been demonstrated that the most aggressive of these sulfur-bearing gases is elemental sulfur ($S_8$).

Corrosion of metal conductors caused by sulfur components in the air is especially severe when one or more of the metal conductors is/are a silver-containing metal. Such silver-containing metal conductors are frequently used in electronic devices to electrically connect electronic components. Examples include the silver layer of gate resistors, described below, and many lead-free solders (e.g., Sn—Ag—Cu solder).

A data center is a facility used to house numerous computer systems and various associated systems, such as data storage systems and telecommunications systems. Data centers typically include redundant/backup power supplies, redundant data communications connections, environmental controls (e.g., HVAC, fire suppression, and the like) and security systems. Data centers are also known as "server farms" due to the large number of computer systems (e.g., servers) typically housed within these facilities.

Typically, the environment of a data center is not monitored for the specific nature of gaseous components. This leaves two options: 1) assume that the data center is relatively clean (i.e., the data center environment is MFG Class I or MFG Class II); or 2) harden the electronic components of the computer systems and the various associated systems housed in the data center. The former option (option 1) leaves at risk the computer systems and the various associated systems housed within the data center. The latter option (option 2) drives additional cost (via the purchase of hardened components or use of conformal coatings which provide some level of protection).

With regard to hardening solutions, it is known to cover metal conductors with a conformal coating to protect the metal conductors from corrosion. For example, U.S. Pat. No. 6,972,249 B2, entitled "Use of Nitrides for Flip-Chip Encapsulation", issued Dec. 6, 2005 to Akram et al., discloses a semiconductor flip-chip that is sealed with a silicon nitride layer on an active surface of the flip-chip. U.S. patent application Ser. No. 12/696,328, entitled "Anti-Corrosion Conformal Coating for Metal Conductors Electrically Connecting an Electronic Component", filed Jan. 29, 2010 by Boday et al., discloses a conformal coating that comprises a polymer into which a phosphine compound is impregnated and/or covalently bonded. The phosphine compound in the polymer reacts with any corrosion inducing sulfur component in the air and prevents the sulfur component from reacting with the underlying metal conductors. However, as mentioned above, a key disadvantage with such hardening solutions is cost.

As mentioned above, the problem of corrosion caused by sulfur components (e.g., elemental sulfur, hydrogen sulfide, and/or sulfur oxides) in the air is especially severe when one or more of the metal conductors that electrically connect an electronic component is/are a silver-containing metal. For example, each of the gate resistors of a resistor network array typically utilizes a silver layer at each of the gate resistor's terminations. Gate resistors are also referred to as "chip resistors" or "silver chip resistors". Typically, gate resistors are coated with a glass over coat for corrosion protection. Also for corrosion protection, it is known to encapsulate gate resistors in a resistor network array by applying a coating of a conventional room temperature-vulcanizable (RTV) silicone rubber composition over the entire printed circuit board on which the resistor network array is mounted. However, the glass over coat and conventional RTV silicone rubber compositions fail to prevent or retard sulfur components in the air from reaching the silver layer in gate resistors. Hence, any sulfur components in the air will react with the silver layer in the gate resistor to form silver sulfide. This silver sulfide formation often causes the gate resistor to fail, i.e., the formation of silver sulfide, which is electrically non-conductive, produces an electrical open at one or more of the gate resistor's terminations.

FIG. 1 illustrates, in an exploded view, an example of a conventional gate resistor 100 of a resistor network array. A resistor element 102 is mounted to a substrate 104, such as a ceramic substrate. The gate resistor 100 includes two termination structures 110, each typically comprising an inner Ag (silver) layer 112, a protective Ni (nickel) barrier layer 114, and an outer solder termination layer 116. Typically, for corrosion protection, the gate resistor 100 is coated with a glass over coat 120. Additionally, for corrosion protection, a coating (not shown) of a conventional RTV silicone rubber composition may encapsulate the gate resistor 100. As noted above, it is known to encapsulate gate resistors in a resistor network array mounted on a printed circuit board by applying a coating of a conventional RTV silicone rubber composition over the entire board. However, as noted above, the glass over coat 120 and conventional RTV silicone rubber compositions fail to prevent or retard sulfur components in the air from reaching the inner silver layer 112. Hence, any sulfur components in the air will react with the inner silver layer 112 to form silver sulfide 202 (shown in FIG. 2). FIG. 2 illustrates, in a sectional view, the conventional gate resistor 100 shown in FIG. 1, but which has failed due to exposure to sulfur-bearing gases. The silver sulfide formation 202 (often referred to as silver sulfide "whiskers") produces an electrical open at one or more of the gate resistor's terminations 110 because silver sulfide is an electrical non-conductor and, thereby, results in failure of the gate resistor 100.

The use of silver as an electrical conductor for electrically connecting electronic components is increasing because silver has the highest electrical conductivity of all metals, even higher than copper. In addition, the concentration of sulfur components in the air is unfortunately increasing as well. Hence, the problem of corrosion caused by sulfur components in the air is expected to grow with the increased use of silver as an electrical conductor for electrically connecting electronic components and the increased concentration of sulfur components in the air.

Traditional mechanisms for monitoring data center corrosive gas concentration have focused on copper (Cu) and silver (Ag) corrosion coupons strategically placed throughout the data center. Both Cu and Ag corrosion coupons react with the corrosive gases and provide a warning either through a visual indication of gas-induced corrosion on the coupon itself or through monitoring the coupon for a change in resistance. However, both of these approaches require significant corrosion of the coupon metallurgy to have occurred before warning is provided. Unfortunately, by the time either of these approaches provides a warning that gas-induced corrosion has occurred with respect to the corrosion coupon, unprotected computer hardware housed in the data center will have already experienced corrosion damage.

Monitors exist for detecting the presence of sulfur oxides and/or hydrogen sulfide in air, but no monitors exist that provide an early warning detection of the presence of elemental sulfur in air.

Therefore, a need exists for an enhanced mechanism for monitoring the air in data centers and other facilities housing computer systems to provide an early warning detection of the presence of corrosive gases, especially elemental sulfur ($S_8$), so that appropriate mitigation can be undertaken.

SUMMARY OF THE INVENTION

An early warning sulfur detection system for detecting the presence of corrosive gases, especially elemental sulfur ($S_8$), in air employs a substrate that includes a polymer-bound phosphine compound having sulfur-getting functionality. The phosphine compound in the polymer reacts with any airborne elemental sulfur. This reaction is accompanied by a decrease in the fluorescence intensity ($I_f$) of the substrate. The $I_f$ of the substrate is monitored in real time by a spectrofluorometer to detect a change in fluorescence intensity ($\Delta I_f$). In an embodiment sited in a data center, an alarm is triggered if the $\Delta I_f$ is above a predetermined threshold, thereby providing a real-time, early warning to IT professionals that corrective action is required to protect metal conductors from corrosion. Preferably, the phosphine compound in the polymer does not react with other components in the air (e.g., carbon dioxide).

BRIEF DESCRIPTION OF THE DRAWINGS

The preferred exemplary embodiments of the present invention will hereinafter be described in conjunction with the appended drawings, where like designations denote like elements.

DETAILED DESCRIPTION OF THE PREFERRED EMBODIMENTS

1. Overview

An early warning sulfur detection system for detecting the presence of corrosive gases, especially elemental sulfur ($S_8$), in air employs a substrate that includes a polymer-bound phosphine compound having sulfur-getting functionality. The phosphine compound in the polymer reacts with any airborne elemental sulfur. This reaction is accompanied by a decrease in the fluorescence intensity ($I_f$) of the substrate. The $I_f$ of the substrate is monitored in real time by a spectrofluorometer to detect a change in fluorescence intensity ($\Delta I_f$). In an embodiment sited in a data center, an alarm is triggered if the $\Delta I_f$ is above a predetermined threshold, thereby providing a real-time, early warning to IT professionals that corrective action is required to protect metal conductors from corrosion. Preferably, the phosphine compound in the polymer does not react with other components in the air (e.g., carbon dioxide).

2. Detailed Description

Figure 1:
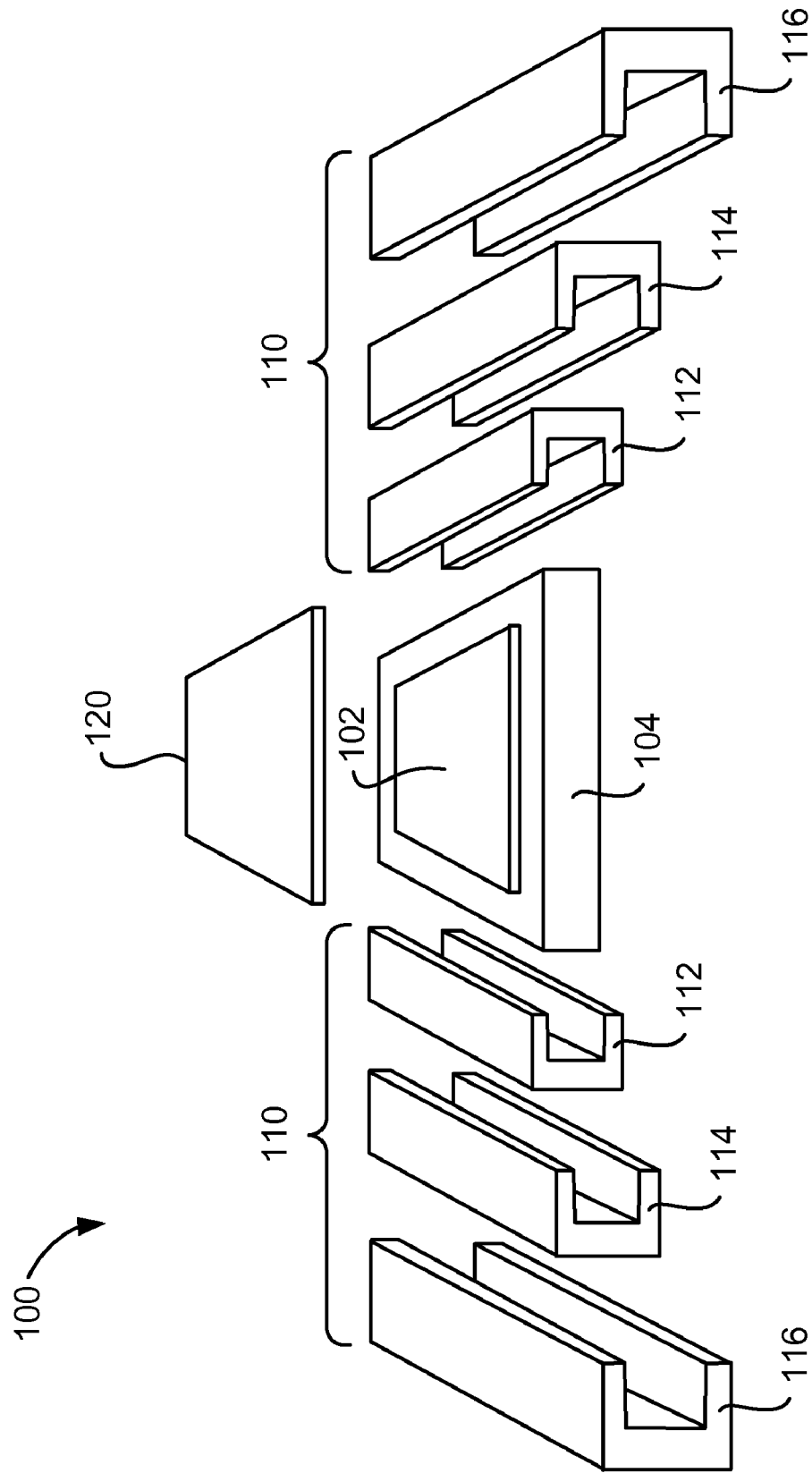
FIG. 1 is an exploded view of a conventional gate resistor of a resistor network array.
Figure 2:
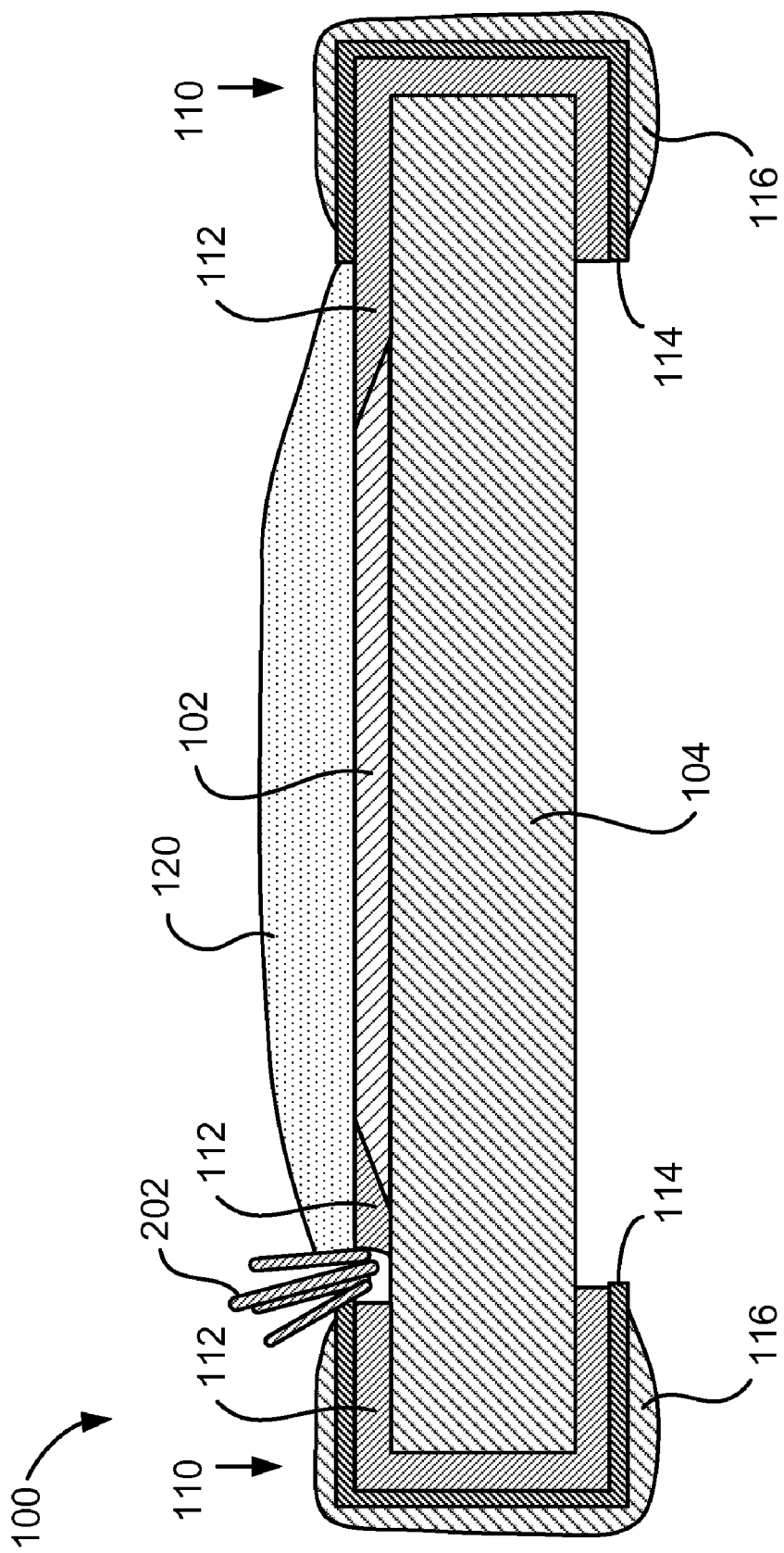
FIG. 2 is a sectional view of the conventional gate resistor shown in FIG. 1, but which has failed due to exposure to sulfur-bearing gases.
Figure 3:
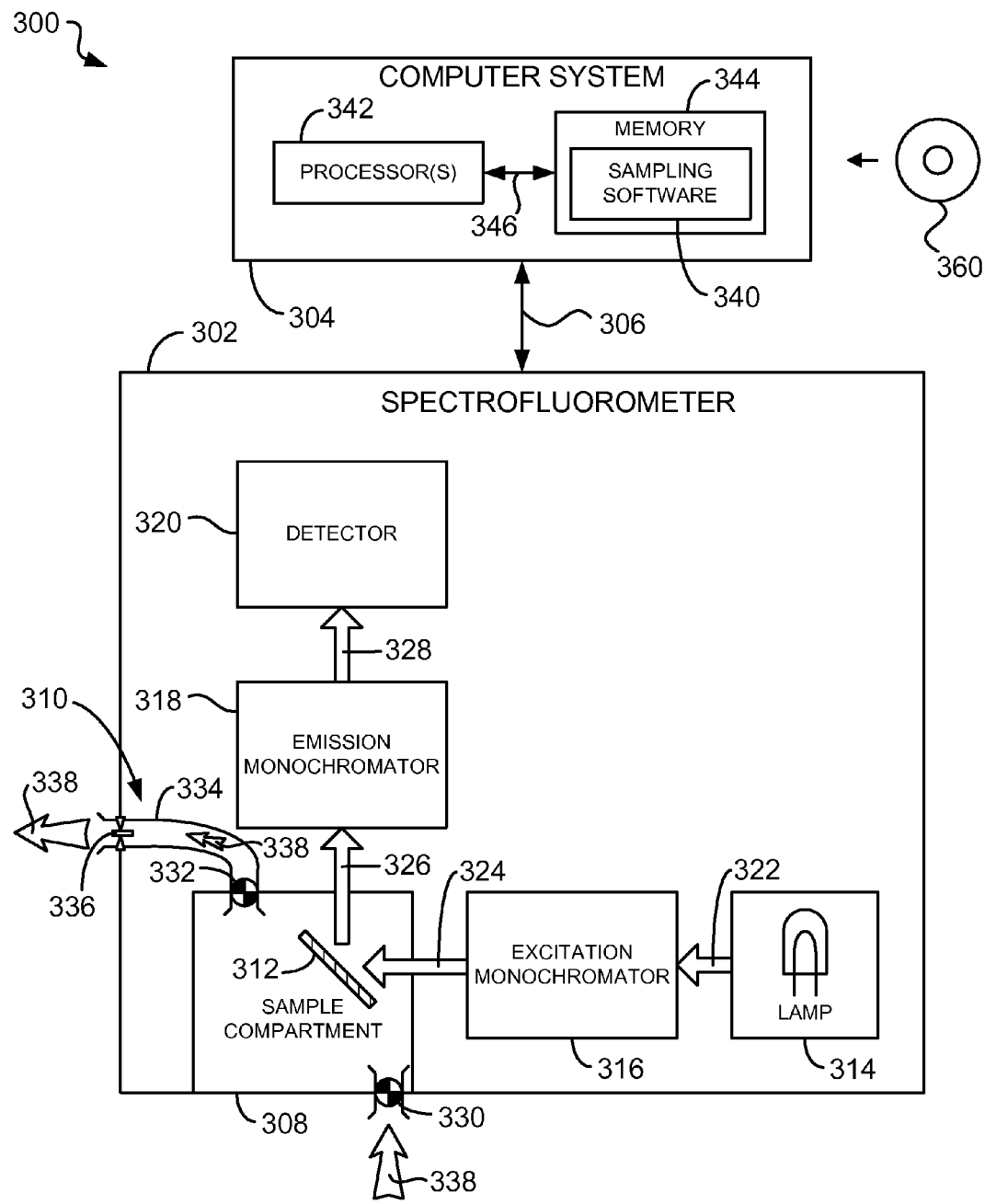
FIG. 3 is a block diagram illustrating a first embodiment of a sulfur detection system for implementing a mechanism for real-time, early warning detection of corrosive gases, especially elemental sulfur ($S_8$), in air based on a change in the fluorescence intensity of a substrate having sulfur-getting functionality in accordance with the present invention.

FIG. 3 is a block diagram illustrating a first embodiment of a sulfur detection system 300 for implementing a mechanism for real-time, early warning detection of corrosive gases, especially elemental sulfur ($S_8$), in air based on a change in the fluorescence intensity of a substrate having sulfur-getting functionality in accordance with the present invention. In the embodiment illustrated in FIG. 3, the sulfur detection system 300 includes as its major components a spectrofluorometer 302 and a computer system 304, which are operatively connected in a conventional manner across a network 306. Alternatively, the spectrofluorometer 302 and the computer system 304 may be integrated into a single unit.

In the embodiment illustrated in FIG. 3, the spectrofluorometer 302 is a standalone-type spectrofluorometer. Alternatively, the spectrofluorometer utilized in accordance with the preferred embodiments of the present invention may be a modular-type spectrofluorometer (e.g., the fiber optic spectrofluorometer 402 illustrated in FIG. 4, described below) that operates in conjunction with accessories, such as a light source unit and a sampling unit.

Generally, spectrofluorometers utilize the fluorescent properties that some materials exhibit in order to provide information about a sample, such as the sample's chemical makeup and/or the concentration of one or more components in the sample. Typically, a certain excitation wavelength is selected to excite the sample, and the emission (i.e., fluorescence intensity) from the sample is detected either at a single wavelength or a scan over a range of wavelengths is performed to obtain the sample's emission spectra, i.e., the fluorescence intensity versus wavelength. Typically, both the excitation wavelength and the detection wavelength are within the range of 200-1100 nm.

The spectrofluorometer 302 is largely conventional except that it includes a sample compartment 308 that is modified to include a shutter system 310, described below. The spectrofluorometer 302 may be, for example, a modified version of the FluoroMax-4 spectrofluorometer, available from HORIBA Jobin Yvon Inc., Edison, N.J.

Also, the sample compartment 308 is modified to include a conventional solid sample holder accessory (not shown) to accommodate a substrate 312, described below, which in accordance with the preferred embodiments of the present invention includes a polymer-bound phosphine compound having sulfur-getting functionality. The solid sample holder may be, for example, the 1933 Solid-Sample Holder accessory, available from HORIBA Jobin Yvon Inc., Edison, N.J.

As is conventional, the spectrofluorometer 302 typically includes a lamp 314, an excitation monochromator 316, an emission monochromator 318, and a detector 320. These components are only briefly discussed below because they are conventional.

As is also conventional, the spectrofluorometer 302 typically includes hardware, software and firmware that are not illustrated in FIG. 3 to communicate with and control internal components, and to provide network connectivity capabilities for the spectrofluorometer 302 to connect with the computer system 304 and other digital computing devices. Such hardware, software and firmware may include one or more network interfaces, one or more processors, and memory.

The networking mechanism used to connect the spectrofluorometer 302 to the computer system 304 typically depends on the network connectivity capabilities of the spectrofluorometer 302. For example, the network connection 306 may be a USB cable, a wireless connection, or an Internet connection.

The present invention applies equally no matter how the computer system 304 may be connected to the spectrofluorometer 302, regardless of whether the network connection 306 is made using present-day analog and/or digital techniques or via some networking mechanism of the future. In addition, many different network protocols can be used to implement network 306. These protocols are specialized computer programs that allow computers to communicate across network 306. TCP/IP (Transmission Control Protocol/Internet Protocol) is an example of a suitable network protocol.

The lamp 314 is typically a xenon (Xe) lamp, but may be any suitable high intensity light source. A high intensity light source is typically selected as the lamp 314 in order to bombard the substrate 312 with as many photons as possible and, thereby, maximize the number of molecules in the substrate 312 that enter the excited state. The light 322 produced by the lamp 314 is typically focused on an entrance-slit of the excitation monochromator 316 using an elliptical mirror (not shown).

The light 322 received from the lamp 314 is passed through the excitation monochromator 316, the purpose of which is to allow selection of an excitation wavelength to use as the excitation light 324. As is conventional, the excitation wavelength is selected by the user through interaction with the sampling software 340. Alternatively, the light 322 produced by the lamp 314 may be passed through a filter to select a fixed excitation wavelength in lieu of, or in addition to, being passed through an excitation monochromator.

The excitation light 324 output by the excitation monochromator 316 enters the sample compartment 308 and excites the substrate 312. In the embodiment illustrated in FIG. 3, the fluorescence emission light 326 from the substrate 312 is collected at 90° to the excitation light 324. Because the substrate 312 is a solid, a front-face fluorescence detection technique is used in accordance with the preferred embodiments of the present invention. In front-face detection, the excitation light 324 is focused onto the front surface of the substrate 312 and then the fluorescence emission light 326 is collected from the same region at an angle (e.g., 22.5°, 30°, 60° or 90°) that minimizes reflected and scattered light.

The fluorescence emission light 326 is passed through the emission monochromator 318, the purpose of which is to allow selection of a single emission wavelength or range of emission wavelengths for an emission spectrum, before being detected as emission light 328 by the detector 320. As is conventional, the emission wavelength or range of emission wavelengths is selected by the user though interaction with the sampling software 340. Alternatively, the fluorescence emission light 326 may be passed through a filter to select a fixed emission wavelength or range of emission wavelengths in lieu of, or in addition to, being passed through an emission monochromator.

The detector 320 collects the emission light 328 received from the emission monochromator 318 and converts the optical signal to an analog signal or a digital signal. As is conventional, this signal is passed onto the sampling software 340 for processing. Although the signal can be processed as a digital or analog signal, a digital signal is typically preferable. The detector 320 may be any suitable detector, such as a PMT, photodiode, or CCD detector. As is conventional, the detector 320 may employ photon-counting for low-light-level detection. Photon counting concentrates on signals originating from fluorescence photons and may be selected by the user through interaction with the sampling software 340.

In the embodiment illustrated in FIG. 3, the spectrofluorometer 302 transmits optical signals through free space. Alternatively, a spectrofluorometer utilized in accordance with the preferred embodiments of the present invention may transmit optical signals through optical fibers (or a combination of optical fibers and free space). For example, the spectrofluorometer utilized in accordance with the preferred embodiments of the present invention may use a fluorescence probe (e.g., the fiber optic fluorescence probe 410 illustrated in FIG. 4, described below) that routes excitation and emission optical fibers through a single probe. In such an alternative embodiment, the fluorescence probe may project into the sample compartment 308 and may be positioned so that the terminal end of the probe is in close contact or proximity to the substrate 312.

Figure 4:
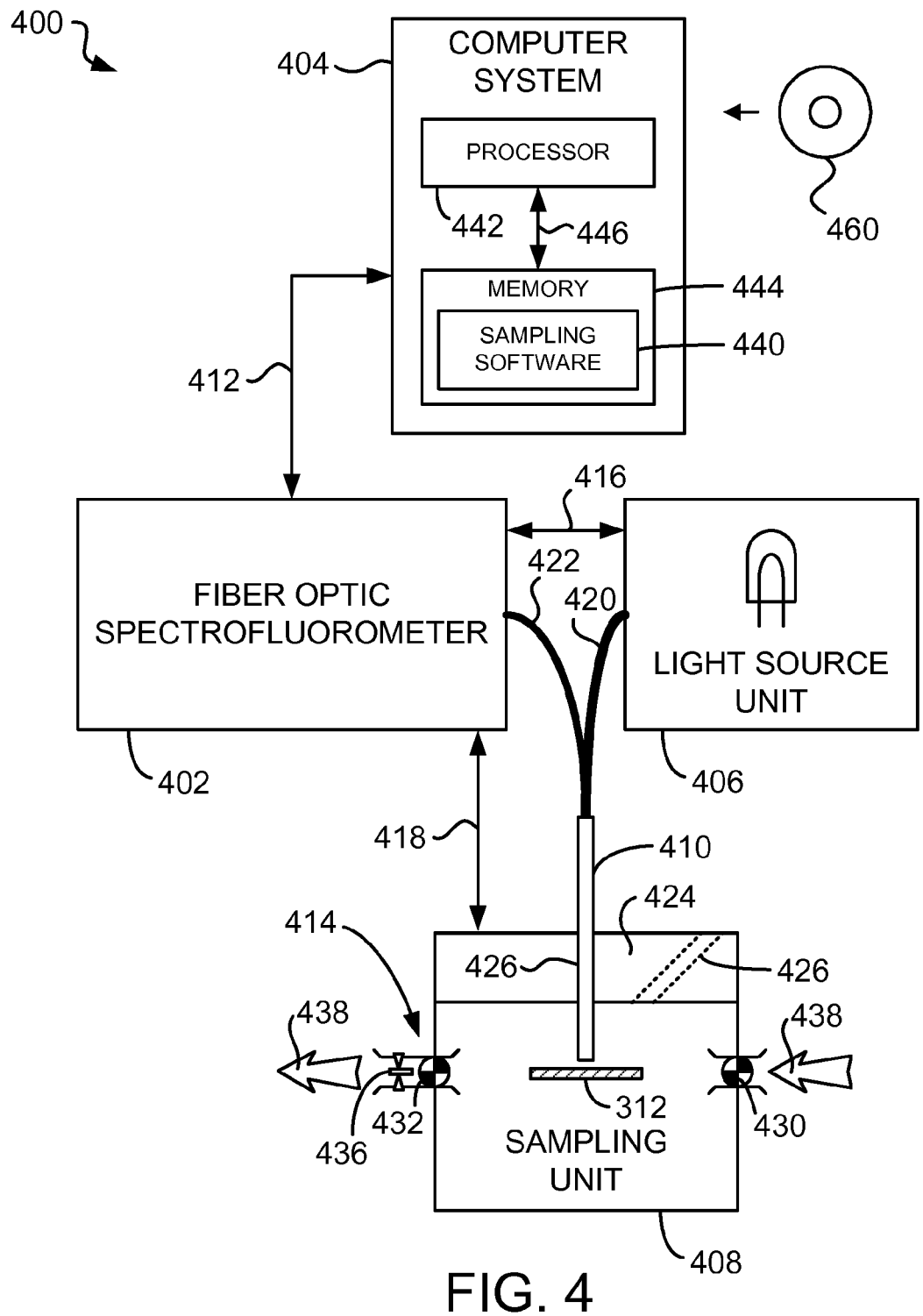
FIG. 4 is a block diagram illustrating a second embodiment of a sulfur detection system for implementing a mechanism for real-time, early warning detection of corrosive gases, especially elemental sulfur ($S_8$), in air based on a change in the fluorescence intensity of a substrate having sulfur-getting functionality in accordance with the present invention.

More generally, the particular configurations of the optical signal pathways illustrated in FIG. 3 and FIG. 4 are exemplary and for purposes of illustrating the preferred embodiments of the present invention and, hence, the particular configurations illustrated therein are not limiting.

The sample compartment 308 is largely conventional except that it is modified to include the shutter system 310, described below. Also, as mentioned above, the sample compartment 308 is modified to include a conventional solid sample holder accessory to accommodate a substrate 312, described below, which in accordance with the preferred embodiments of the present invention includes a polymer-bound phosphine compound having sulfur-getting functionality. Typically, the sample compartment 308 includes a hinged lid (not shown) through which the substrate 312 may be inserted and withdrawn from the sample compartment 308.

The interior of the sample compartment 308 is preferably black to minimize stray light. For example, the interior of the sample compartment 308, including its hinged lid, may be painted black. Also in order to minimize stray light, conventional sample compartments are typically sealed except for slits through which the excitation and emission light passes. In accordance with the preferred embodiments of the present invention, the sample compartment 308 is provided with the shutter system 310, which selectively provides a pathway for air from the surrounding environment to enter the sample compartment 308.

The shutter system 310 closes the sample compartment 308 from the surrounding environment during measurements of the fluorescence intensity of the substrate 312 and opens the sample compartment 308 to the surrounding environment during periods between the measurements. In the embodiment illustrated in FIG. 3, the shutter system 310 includes an air intake door 330, an air exhaust door 332, an air exhaust duct 334, and an air exhaust fan 336.

In the embodiment illustrated in FIG. 3, when the air intake and exhaust doors 330 and 332 are open, air from the environment surrounding the spectrofluorometer 302 is drawn by the exhaust fan 336 through the intake door 330, through the sample compartment 308, through the exhaust door 332, and through the exhaust duct 334. The air drawn into the sample compartment 308 by the exhaust fan 336 is then exhausted back to the surrounding environment. Airflow is represented in FIG. 3 by arrows denoted as 338.

However, the particular components used in and configurations of the air pathways illustrated in FIG. 3 and FIG. 4 are exemplary and for purposes of illustrating the preferred embodiments of the present invention and, hence, the particular components and configurations illustrated therein are not limiting.

In the embodiment illustrated in FIG. 3, the air intake and exhaust doors 330 and 332 are provided by a pair of conventional two-port solenoid valves, which may be controlled by the sampling software 340. A solenoid valve is an electromechanical valve for use with liquids or gases. Typically, a solenoid valve includes an actuator (e.g., a plunger-type actuator, a pivoted-armature actuator, or a rocker actuator) that is controlled by an electric current through a solenoid coil. In a two-port solenoid valve, flow of the liquid or gas is switched on or off by the actuator depending on whether or not current is flowing through the solenoid coil. Those skilled in the art will appreciate, however, that these doors may take other forms. For example, these doors may be provided by a series of light-blocking baffles that allow air to freely flow through the sample compartment 308.

Preferably, the air intake door 330, the air exhaust door 332, and the air exhaust fan 336 are controlled by the sampling software 340, as described further below with reference to FIG. 5. In accordance with the preferred embodiments of the present invention, the sampling software 340 closes the air intake door 330 and the air exhaust door 332 and turns off the air exhaust fan 336 before each measurement of the fluorescence intensity of the substrate 312. During periods between these measurements, the sampling software 340 opens the air intake door 330 and the air exhaust door 332 and turns on the air exhaust fan 336.

The computer system 304 is largely conventional except that it includes sampling software 340 that is modified to perform the functions as further described below with reference to FIG. 5. For example, the computer system 304 may be a PC. However, those skilled in the art will appreciate that the method, apparatus, and computer program product of the present invention apply equally to any computer system, regardless of whether the computer system is a complicated multi-user computing apparatus, a PC, or an embedded control system. As shown in FIG. 3, the computer system 304 comprises one or more processors 342 and a main memory 344. These system components, as well as other conventional system components such as a network interface (not shown), are interconnected through a system bus 346.

In the embodiment illustrated in FIG. 3, the sampling software 340 resides in the main memory 344. The sampling software 340 may be, for example, a modified version of the FluorEssence software package, available from HORIBA Jobin Yvon Inc., Edison, N.J., which is data acquisition and modeling software that provides complete control of spectrofluorometer hardware. In accordance with the preferred embodiments of the present invention, the sampling software 340 performs the functions as further described below with reference to FIG. 5.

At this point, it is important to note that while the description above is in the context of a fully functional computer system, those skilled in the art will appreciate that the sampling software 340, as well as other software type entities described herein (e.g., the sampling software 440 in FIG. 4) may be distributed as an article of manufacture (also referred to herein as a "computer program product") in a variety of forms, and the claims extend to all suitable types of computer-readable media used to actually carry out the distribution, including recordable type media such as floppy disks, CD-RWs, CD-ROMS (e.g., CD-ROM 360 in FIG. 3, or CD-ROM 460 in FIG. 4) and DVD-ROMs.

FIG. 4 is a block diagram illustrating a second embodiment of a sulfur detection system 400 for implementing a mechanism for real-time, early warning detection of corrosive gases, especially elemental sulfur ($S_8$), in air based on a change in the fluorescence intensity of a substrate having sulfur-getting functionality in accordance with the present invention. In the embodiment illustrated in FIG. 4, the sulfur detection system 400 includes as its major components a fiber optic spectrofluorometer 402, a computer system 404, a light source unit 406, a sampling unit 408, and a fluorescence probe 410.

In the embodiment illustrated in FIG. 4, the fiber optic spectrofluorometer 402 and the computer system 404 are operatively connected in a conventional manner across a network 412. Alternatively, the fiber optic spectrofluorometer 402 and the computer system 404 may be integrated into a single unit.

Also in the embodiment illustrated in FIG. 4, the light source unit 406 and the sampling unit 408 are operatively connected to the fiber optic spectrofluorometer 402 across networks 416 and 418, respectively. In this regard, conventional fiber optic spectrofluorometers typically include an accessory connector (not shown) for controlling one or more accessories such as the light source unit 406 and the sampling unit 408. Alternatively, the light source unit 406 and/or the sampling unit 408 may be operatively connected to the computer system 404 across one or more networks (in lieu of, or in addition to, the networks 416 and 418).

The fiber optic spectrofluorometer 402 is conventional, as are the light source unit 406 and the fluorescence probe 410. The fiber optic spectrofluorometer 402 may be, for example, the USB2000FLG Fiber Optic Gated Spectrometer or the USB2000 Fiber Optic Spectrometer, each available from Ocean Optics Inc., Dunedin, Fla. The light source unit 406 may be, for example, the PX-2 Pulsed Xenon Light Source, available from Ocean Optics Inc., Dunedin, Fla. The fluorescence probe 410 may be, for example, the QF600-8-VIS/NIR Fiber Fluorescence Probe, available from Ocean Optics Inc., Dunedin, Fla.

The sampling unit 408 includes a conventional solid sample holder accessory (not shown) to accommodate a substrate 312, described below, which in accordance with the preferred embodiments of the present invention includes a polymer-bound phosphine compound having sulfur-getting functionality. The solid sample holder may be, for example, the 1933 Solid-Sample Holder accessory, available from HORIBA Jobin Yvon Inc., Edison, N.J.

The light source unit 406 typically includes components (not shown) that generally correspond to the lamp 314 and the excitation monochromator 316 described above with respect to FIG. 3.

The fiber optic spectrofluorometer 402 typically includes components (not shown) that generally correspond to the emission monochromator 318 and the detector 320 described above with respect to FIG. 3. As is also conventional, the fiber optic spectrofluorometer 402 typically includes hardware, software and firmware to communicate with and control accessories (e.g., the light source unit 406 and the sampling unit 408), and to provide network connectivity capabilities for the fiber optic spectrofluorometer 402 to connect with the computer system 404 and other digital computing devices. Such hardware, software and firmware may include one or more network interfaces, one or more processors, and memory.

The networking mechanism used to connect the fiber optic spectrofluorometer 402 to the computer system 404 typically depends on the network connectivity capabilities of the fiber optic spectrofluorometer 402. For example, the network connection 412 may be a USB cable, a wireless connection, or an Internet connection.

The present invention applies equally no matter how the computer system 404 may be connected to the fiber optic spectrofluorometer 402, regardless of whether the network connection 412 is made using present-day analog and/or digital techniques or via some networking mechanism of the future. In addition, many different network protocols can be used to implement network 412. These protocols are specialized computer programs that allow computers to communicate across network 412. TCP/IP (Transmission Control Protocol/Internet Protocol) is an example of a suitable network protocol.

The fluorescence probe 410 includes a one or more excitation fibers 420 (typically, six or seven angled polished excitation fibers) and one or more fluorescence emission collection fibers 422 (typically, one flat polished emission fiber). In a typical example, the fluorescence probe 410 is terminated in a pen-like rod with a single collection fiber surrounded by six or seven excitation fibers. A lens at the terminal end of the fluorescence probe 410 is used to deliver the excitation light to the substrate 312 and collect the fluorescence emission light from the substrate 312. The terminal end of the fluorescence probe end 410 can be placed in close contact or proximity to the substrate 312.

The excitation light output by the light source unit 406 enters the one or more angled excitation fibers 420 and excites the substrate 312. The fluorescence emission light from the substrate 312 is collected by the one or more collection fibers 422. Because the substrate 312 is a solid, a front-face fluorescence detection technique is used in accordance with the preferred embodiments of the present invention. In front-face detection, the excitation light is focused to the front surface of the substrate 312 and then the fluorescence emission light is collected from the same region at an angle (e.g., 22.5°, 30°, 60° or 90°) that minimizes reflected and scattered light. Hence, the excitation fibers 420 are typically "angled" polished, while the emission fiber 422 is "flat" polished.

In the embodiment illustrated in FIG. 4, the fluorescence probe is mounted so that its pen-like rod extends at an angle normal (90°) to the front surface of the substrate 312. In order to minimize reflection and scattered light, the sampling unit 408 may include a fluorescence probe mounting block 424 having a series of mounting holes 426, any one of which the fluorescence probe 410 may pass. This provides the capability of mounting the fluorescence probe 410 at various angles (e.g., 30°, 45°, 60° or 90°) relative to the front surface of the substrate 312.

The fiber optic spectrofluorometer 402 receives the fluorescence emission light from the one or more collection fibers 422 of the fluorescence probe 410 and converts the optical signal to an analog signal or a digital signal. As is conventional, this signal is passed onto the sampling software 440 for processing. Although the signal can be processed as a digital or analog signal, a digital signal is typically preferable.

The sampling unit 408 includes a shutter system 414. Also, as mentioned above, the sampling unit 408 includes a conventional solid sample holder accessory to accommodate a substrate 312, described below, which in accordance with the preferred embodiments of the present invention includes a polymer-bound phosphine compound having sulfur-getting functionality. As is conventional, the sampling unit 408 preferably includes a hinged lid (not shown) through which the substrate 312 may be inserted and withdrawn from the sampling unit 408.

The interior of the sampling unit 408 is preferably black to minimize stray light. For example, the interior of the sampling unit 408, including its hinged lid, may be painted black. Also in order to minimize stray light, conventional sampling units are typically sealed. In accordance with the preferred embodiments of the present invention, the sampling unit 408 is provided with the shutter system 414, which selectively provides a pathway for air from the surrounding environment to enter the sampling unit 408.

The shutter system 414 closes the sampling unit 408 from the surrounding environment during measurements by the fiber optic spectrofluorometer 402 of the fluorescence intensity of the substrate 312 and opens the sampling unit 408 to the surrounding environment during periods between the measurements. In the embodiment illustrated in FIG. 4, the shutter system 414 includes an air intake door 430, an air exhaust door 432, and an air exhaust fan 436.

In the embodiment illustrated in FIG. 4, when the air intake and exhaust doors 430 and 432 are open, air from the environment surrounding the fiber optic spectrofluorometer 402 is drawn by the exhaust fan 436 through the intake door 430, through the sampling unit 408, and through the exhaust door 432. The air drawn into the sampling unit 408 by the exhaust fan 436 is then exhausted back to the surrounding environment. Airflow is represented in FIG. 4 by arrows denoted as 438.

In the embodiment illustrated in FIG. 4, the air intake and exhaust doors 430 and 432 are provided by a pair of conventional two-port solenoid valves, which may be controlled by the sampling software 440. A solenoid valve is an electromechanical valve for use with liquids or gases. Typically, a solenoid valve includes an actuator (e.g., a plunger-type actuator, a pivoted-armature actuator, or a rocker actuator) that is controlled by an electric current through a solenoid coil. In a two-port solenoid valve, flow of the liquid or gas is switched on or off by the actuator depending on whether or not current is flowing through the solenoid coil. Those skilled in the art will appreciate, however, that these doors may take other forms. For example, these doors may be provided by a series of light-blocking baffles that allow air to freely flow through the sampling unit 408.

Preferably, the air intake door 430, the air exhaust door 432, and the air exhaust fan 436 are controlled by the sampling software 440, as described further below with reference to FIG. 5. In accordance with the preferred embodiments of the present invention, the sampling software 440 closes the air intake door 430 and the air exhaust door 432 and turns off the air exhaust fan 436 before each measurement of the fluorescence intensity of the substrate 312. During periods between these measurements, the sampling software 440 opens the air intake door 430 and the air exhaust door 432 and turns on the air exhaust fan 436.

The computer system 404 is largely conventional except that it includes sampling software 440 that is modified to perform the functions as further described below with reference to FIG. 5. For example, the computer system 404 may be a PC. However, those skilled in the art will appreciate that the method, apparatus, and computer program product of the present invention apply equally to any computer system, regardless of whether the computer system is a complicated multi-user computing apparatus, a PC, or an embedded control system. As shown in FIG. 4, the computer system 404 comprises one or more processors 442 and a main memory 444. These system components, as well as other conventional system components such as a network interface (not shown), are interconnected through a system bus 446.

In the embodiment illustrated in FIG. 4, the sampling software 440 resides in the main memory 444. The sampling software 440 may be, for example, a modified version of the SpectraSuite or OOIBase32 operating software, each of which is an application program for data acquisition and modeling software that provides complete control of the fiber optic spectrofluorometer hardware and accessories connected thereto. In accordance with the preferred embodiments of the present invention, the sampling software 440 performs the functions as further described below with reference to FIG. 5.

In accordance with the preferred embodiments of the present invention, the substrate 312 includes a polymer-bound phosphine compound having sulfur-getting functionality. The phosphine compound in the polymer reacts with any corrosive sulfur-containing gases in air (e.g., elemental sulfur, hydrogen sulfide, and/or sulfur oxides), especially elemental sulfur ($S_8$).

Preferably, the polymer-bound phosphine compound is bound in a polymer film which is deposited on the surface of a substrate base (e.g., any suitable non-fluorescing material such as quartz). For example, the polymer film may be a phosphine-containing polymer conformal coating as disclosed in U.S. patent application Ser. No. 12/696,328, entitled "Anti-Corrosion Conformal Coating for Metal Conductors Electrically Connecting an Electronic Component", filed Jan. 29, 2010 by Boday et al., which is incorporated herein by reference in its entirety. Alternatively, the substrate may be entirely composed of the polymer and the polymer-bound phosphine compound.

Advantageously, existing deposition processes may be used for applying the conformal coating to the substrate base. Hence, any currently used conformal coating process utilized in the preparation of electronic components may be used to deposit the polymer film onto the substrate base. Numerous processes conformally coat components with polymers. A phosphine compound may be impregnated into and/or covalently bonded to these polymers within the scope of the present invention.

The conformal coating is composed of a polymer into which a phosphine compound is impregnated and/or covalently bonded. The phosphine compound may be, for example, impregnated into the conformal coating by mixing the phosphine compound with the polymer. In this case, the phosphine compound is merely blended in with the polymer (as opposed to being covalently bonded to the polymer). On the other hand, covalently bound sulfur-gettering functionalities (i.e., provided by the phosphine compound) may be advantageous (e.g., for volatile sulfur-gettering species). It may be desirable, for example, to covalently bond the phosphine compound directly into the polymer backbone and, thereby, render the phosphine compound completely nonvolatile Conformal coatings typically fall into one of several generic classes: silicones, epoxies, acrylates, or other organic materials. Hence, the polymer in the conformal coating may be, for example, one or more silicone-based polymers, one or more epoxy-based polymers, one or more acrylate-based polymers, and/or one or more other organic materials; and combinations thereof. For example, the polymer may be the substituted phosphine polysiloxane of formula (1):

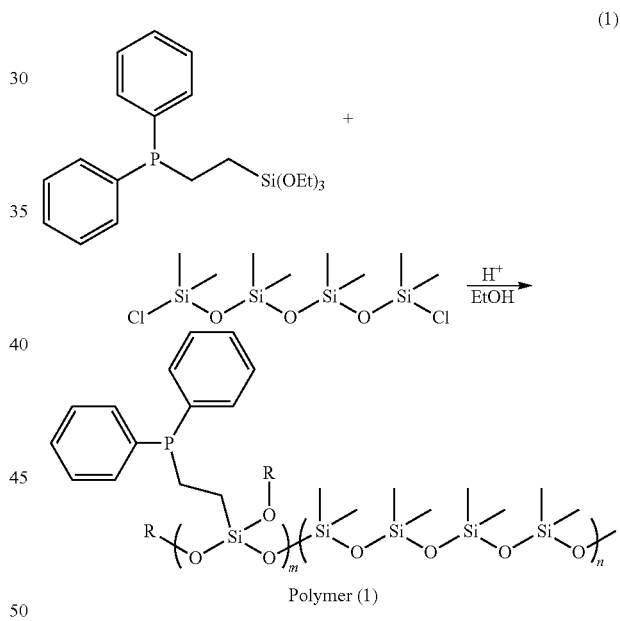

Polymer (1)

wherein each silicon atom in the substituted polysiloxane of polymer (1) is attached to a hydrogen atom, an alkyl group, or an aryl group; and wherein:

R is a hydrogen atom, an alkyl group, or an aryl group, m is an integer of at least 1, and n is an integer of at least 1.

In the foregoing example, the polymer solution may be prepared by reacting a substituted phenyl phosphine [i.e., diphenyl(2-(triethoxysilyl)ethyl)phosphine] and a substituted siloxane [e.g., 1,7-dichlorotetrasiloxane] in acidic solution in the presence of ethanol. Each silicon atom in the substituted siloxane is attached to a hydrogen atom, an alkyl group, or an aryl group.

An example of an epoxy-based polymer that includes a covalently-bound phosphine compound is depicted in formula (2):

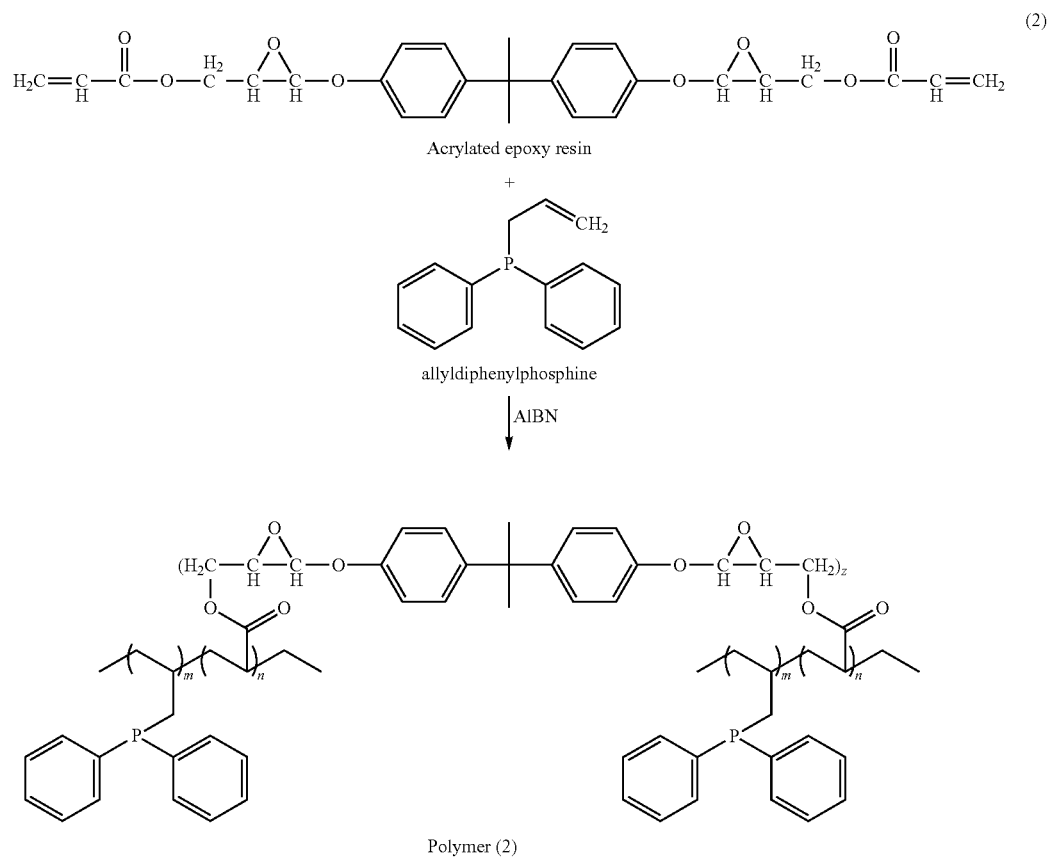

wherein z, m and n are integers of at least 1. In the foregoing example, a commercially available acrylated epoxy is reacted with allyldiphenylphosphine in the presence of AIBN (or some other suitable free radical initiator known to those skilled in the art) to form polymer (2), which is a covalently bound phosphine epoxy resin. For use as a conformal coating, polymer (2) would be reacted with a suitable epoxy crosslinking agent (e.g., photogenerated acid, a Lewis acid, an amine, phenols, etc.) to form the protective coating.

An example of an acrylate-based polymer that includes a covalently-bound phosphine compound is depicted in formula (3):

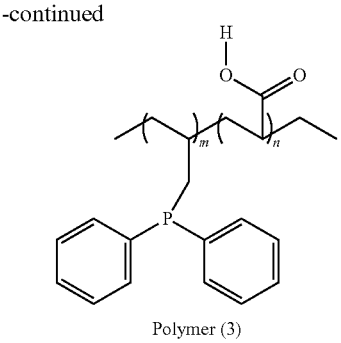

wherein m and n are integers of at least 1. In the foregoing example, allyldiphenylphosphine is reacted with acrylic acid in the presence of AIBN (or some other suitable free radical initiator known to those skilled in the art) to form polymer (3), which is a covalently bound phosphine acrylic resin.

Additional silicone-based polymers (i.e., polymer (4) and polymer (5), below) with covalently-bound phosphine functionality may be synthesized using the following scheme in formulas (4) and (5):

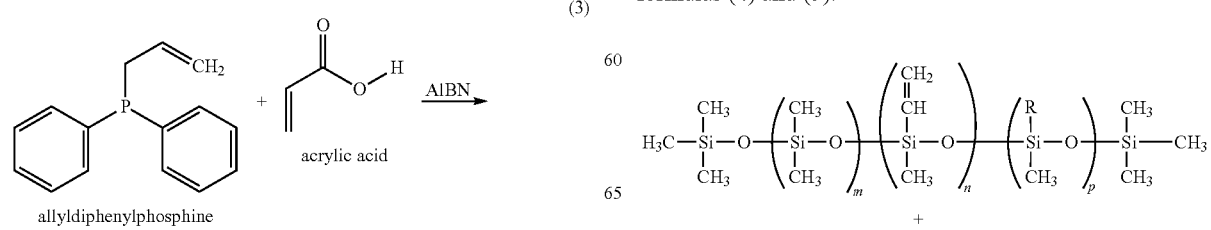

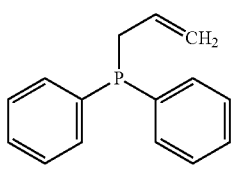

allyldiphenylphosphine

AIBN

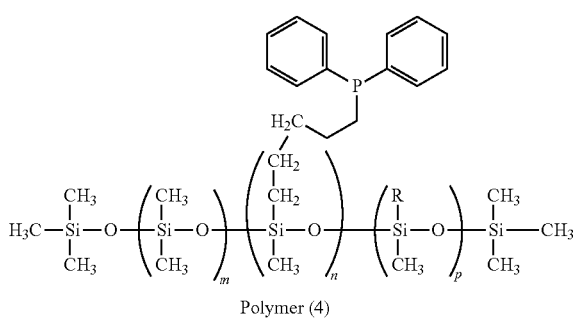

Polymer (4)

(4)
wherein m, n and p are integers of at least 1.

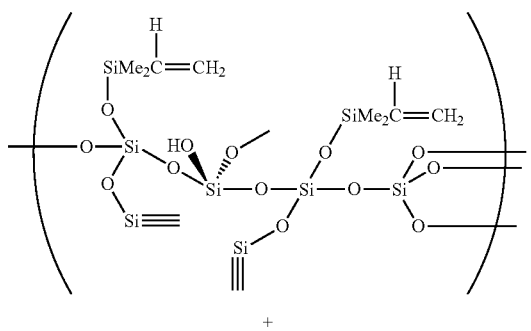

+

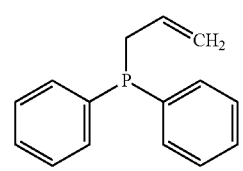

allyldiphenylphosphine

AIBN

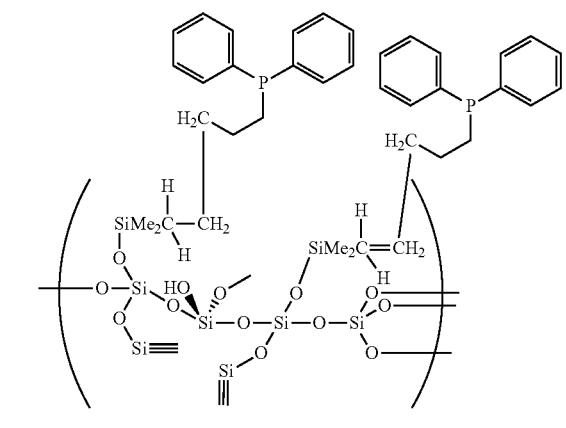

Polymer (5)

(5)

In the foregoing example, allyldiphenylphosphine is reacted with a respective precursor in the presence of AIBN (or some other suitable free radical initiator known to those skilled in the art) to form polymer (4) and polymer (5), respectively, each of which is a covalently bound phosphine polysiloxane.

As noted above, the polymer in the conformal coating may be, for example, one or more silicone-based polymers, one or more epoxy-based polymers, one or more acrylate-based polymers, and/or one or more other organic materials; and combinations thereof. An example of a suitable polymer in the "other organic materials" class of conformal coatings is the polymer depicted in formula (6):

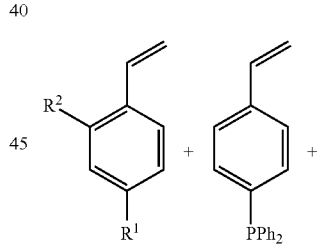

(6)

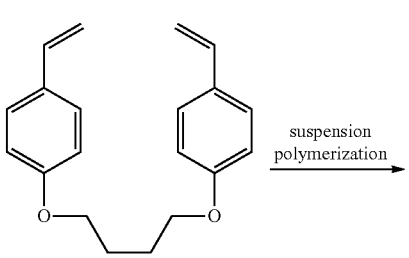

suspension polymerization →

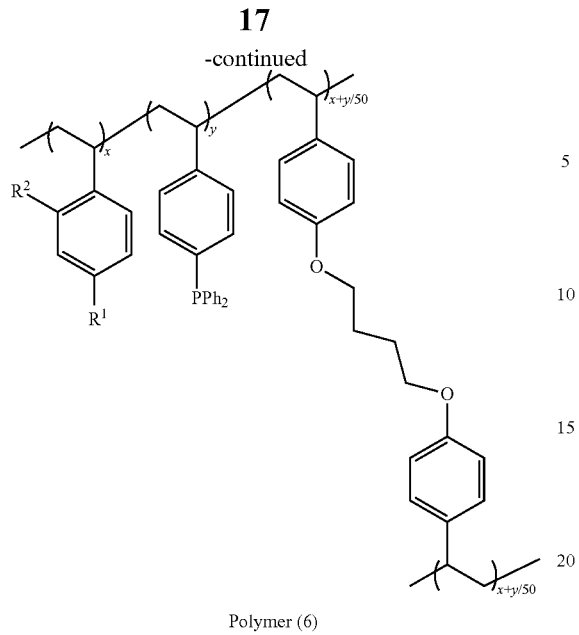

Polymer (6)

wherein:

R¹ is a hydrogen atom, an alcohol, ether, ester, nitrile, or methoxy group,

R² is a hydrogen atom, or methoxy, and x and y are integers of at least 1.

In the foregoing example, triphenylphosphine resins are prepared by suspension polymerization utilizing the materials and procedures disclosed in L.-J. Zhao et al., "Optimization of polystyrene triphenylphosphine catalysts for aza-Morita-Baylis-Hillman reactions", Tetrahedron 61, pages 12026-12032, 2005, Copyright 2005 Elsevier Ltd., which is incorporated herein by reference in its entirety.

The phosphine compound is a sulfur-getter that reacts with the target corrosive species (i.e., sulfur components in the air). The phosphine compound may be, for example, one or more alkyl phosphines and/or one or more aryl phosphines; and combinations thereof. More particularly, the phosphine compound may be one or more substituted or unsubstituted butyl phosphines and one or more substituted or unsubstituted phenyl phosphines; and combinations thereof. For example, the phosphine compound may be a substituted phenyl phosphine of formula (7):

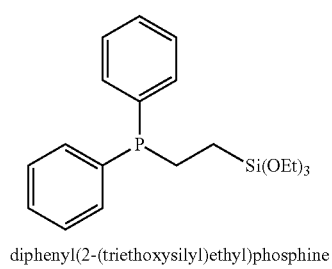

diphenyl(2-(triethoxysilyl)ethyl)phosphine

Additional exemplary phosphine compounds are depicted in the following formulas (8) and (9):

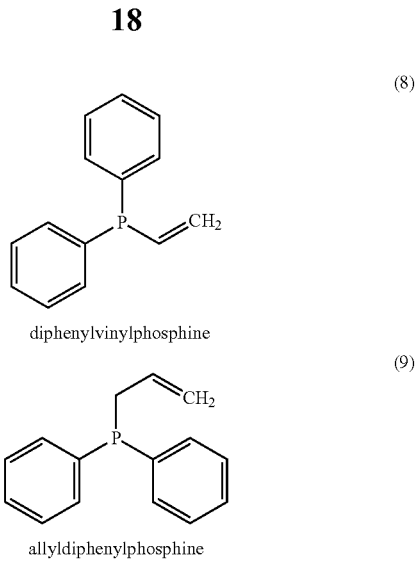

diphenylvinylphosphine allyldiphenylphosphine

Below is a list of other examples of phosphine containing compounds which are capable of becoming covalently linked into the conformal coating using the most common conformal coatings:

(4-Hydroxyphenyl)diphenylphosphine;
2-(Diphenylphosphino)ethylamine;
3-(Diphenylphosphino)-1-propylamine;
Diallylphenylphosphine;
Diphenylphosphinostyrene;
Triallylphenylphosphine;
2-(Diphenylphosphino)ethyl-trimethoxysilane.

It will be appreciated by those skilled in the art that, in accordance with the preferred embodiments of the present invention, the intent is to covalently bind a phosphine-functional group into a polymer backbone to provide the sulfur-getting feature of the conformal coating. As such, numerous phosphine derivatives or phosphine oxide derivatives can be envisaged that will accomplish the intended task. The foregoing examples are merely representative of the synthetic scheme utilized to create the polymer of interest.

In yet another embodiment, phosphine containing compounds such as triphenylphosphine, Dicyclohexyl(2-methylphenyl)phosphine, 4-(Dimethylamino)phenyldiphenylphosphine, Tribenzylphosphine, Benzyldiphenylphosphine, Cyclohexyldiphenylphosphine, and Bis(2-methoxyphenyl)phenylphosphine can be impregnated into a conformal coating such as polysiloxanes, polyepoxide and polyacrylates. The concentration of the phosphine containing compounds which would be impregnated into the conformal coating could range from 0.01-20 wt %, preferably 0.1-10 wt % and most preferably 0.5-5 wt %. The above-listed exemplary phosphine containing compounds, conformal coatings and concentrations are set forth for the purpose of illustration, not limitation. Those skilled in the art will appreciate that other phosphine containing compounds, conformal coatings, and/or concentrations may be used within the scope of the present invention.

The gettering functionality of the phosphine compound binds and traps the target corrosive species (i.e., sulfur components in the air). The phosphine compound, being a sulfur-getter, works by attacking the sulfur-sulfur bond in the corrosive species, breaking it and remaining covalently bonded to it. Hence the corrosive species is trapped on the substrate.

Preferably, the phosphine compound in the polymer does not react with non-sulfur components in the air (e.g., carbon dioxide) which would otherwise deplete the availability of the phosphine compound for the target reaction (i.e., reaction with sulfur components in the air) and possibly compromise the usefulness of the fluorescence measurement for sulfur detection.

In accordance with the preferred embodiments of the present invention, a polymer solution containing a phosphine compound is applied onto the surface of the substrate base. Preferably, the polymer solution is applied in an at least partially uncured state by dipping, spraying, spin-coating, casting, brushing, rolling, syringe, or any other suitable deposition process. Then, the polymer solution is cured to thereby produce the conformal coating. Generally, the process used to cure the polymer solution will vary based on the particular polymer solution used. For example, the polymer solution may be cured in a conventional drying process.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM) (e.g., memory 344 in FIG. 3, or memory 444 in FIG. 4), a read-only memory (ROM), an erasable programmable read-only memory (EPROM or Flash memory), an optical fiber, a portable compact disc read-only memory (CD-ROM) (e.g., CD-ROM 360 in FIG. 3, or CD-ROM 460 in FIG. 4), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc. or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer (e.g., processor 342 of computer system 304 in FIG. 3, or processor 442 of computer system 404 in FIG. 4), special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 5:
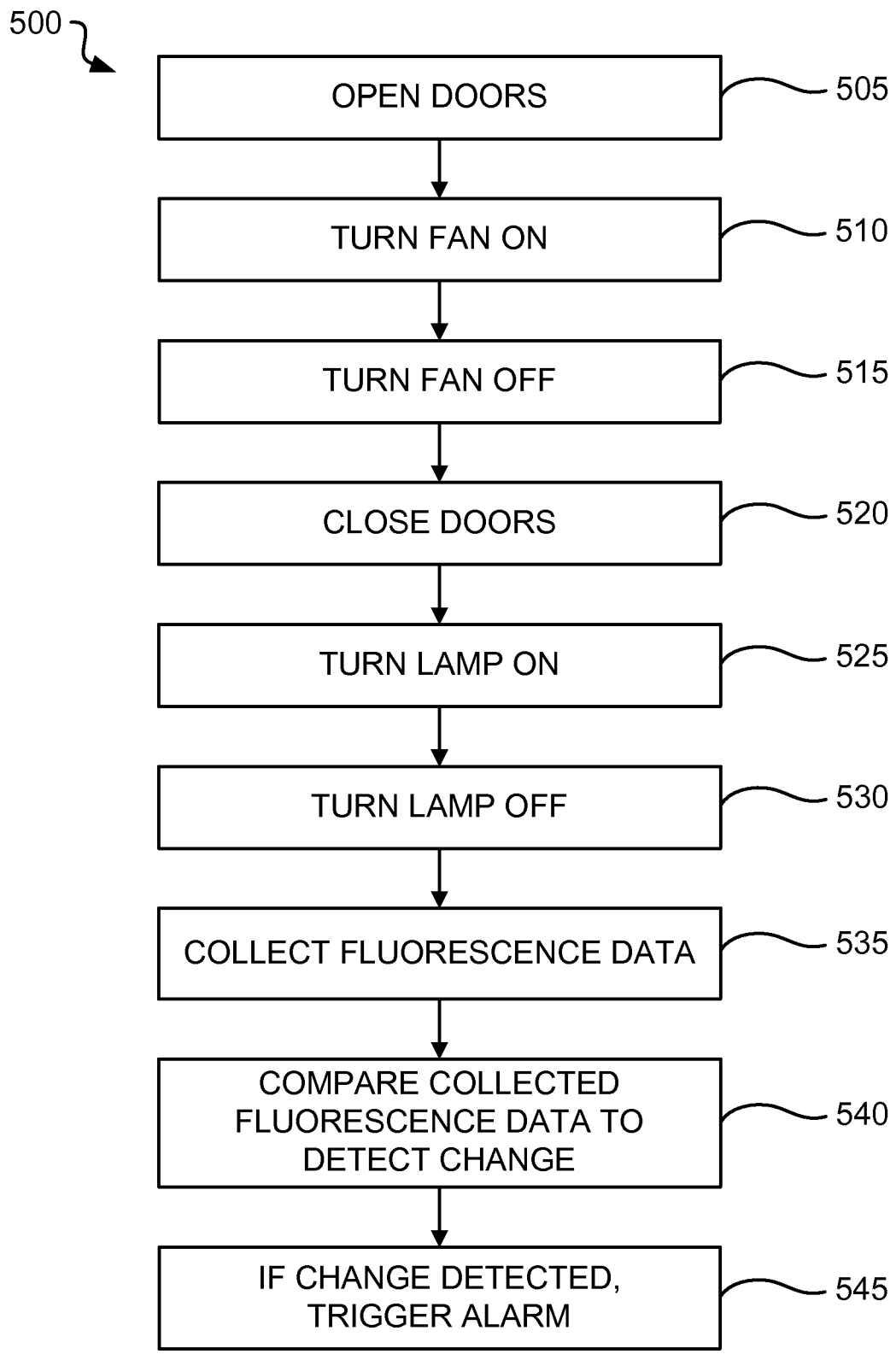
FIG. 5 is a flow chart diagram of a method for real-time, early warning detection of corrosive gases, especially elemental sulfur ($S_8$), in air based on a change in the fluorescence intensity of a substrate having sulfur-getting functionality in accordance with the present invention.

FIG. 5 is a flow chart diagram of a method 500 for real-time, early warning detection of corrosive gases, especially elemental sulfur ($S_8$), in air based on a change in the fluorescence intensity of a substrate having sulfur-getting functionality in accordance with the present invention. Method 500 sets forth the preferred order of steps. It must be understood, however, that the various steps may occur simultaneously or at other times relative to one another. Method 500 begins by opening the doors of the shutter system (step 505). This opens the sample compartment (or the sampling unit) to air from the surrounding environment. For example, step 505 may be performed by activating the solenoid valves that comprise the air intake and exhaust doors. These doors are only open during periods between measurements of the fluorescence intensity of the substrate. The fan of the shutter system is also turned on (step 510). Steps 505 and 510 may be performed simultaneously.

After a predetermined period of time, the method 500 continues by turning off the fan of the shutter system (step 515). The doors of the shutter system are also closed (step 520). This closes the sample compartment (or sampling unit) to air and light from the surrounding environment. For example, step 520 may be performed by deactivating the solenoid valves that comprise the air intake and exhaust doors. Steps 515 and 520 may be performed simultaneously.

The method 500 continues by turning on the lamp (step 525). Excitation light from the excitation monochromator (or light source unit) then enters the sample compartment (or sampling unit) and excites the substrate 312. After a predetermined amount of time, the lamp is turned off (step 530). This predetermined period of time is typically a single strobe. Then, the fluorescence data is collected (step 535).

Preferably, the spectrofluorometer (or fiber optic spectrofluorometer) operates in a conventional "gated fluorescence mode". In the gated fluorescence mode, the spectrofluorometer only detects fluorescence emission light when the lamp is off. To operate in the gated fluorescent mode, the user interacts with the sampling software to select a delay (e.g., 5-500 μsec) between the lamp turning on and the start of the integration period of the spectrofluorometer (i.e., the start of the integration period is when the detector first "sees" the fluorescence emission from the substrate). The integration period is typically 5 msec in the gated fluorescent mode; whereas the integration period is typically 5 msec-20 seconds in the normal mode.

The method 500 continues by comparing the collected fluorescence data to detect whether a change in the fluorescence intensity of the substrate has occurred (step 540). For example, step 540 may be performed by comparing the fluorescence intensity ($I_f$) of the substrate to a time zero fluorescence intensity ($I_f 0$) of the substrate recorded earlier, and thereby detect whether a change in fluorescence intensity ($\Delta I_f$) has occurred. If air from the surrounding environment contains minute quantities of elemental sulfur ($S_8$), the fluorescence intensity ($I_f$) of the substrate decreases. Preferably, the change in fluorescence intensity ($\Delta I_f$) is compared to a predetermined threshold to account for measurement baseline fluctuations. The steps 505-540 are repeated to measure the fluorescence intensity ($I_f$) of the substrate as a function of time. If the change in fluorescence intensity ($\Delta I_f$) is above the predetermined threshold, the method 500 triggers an alarm (step 545). For example, the method 500 may trigger an event that notifies an IT professional that corrective action is required to protect metal conductors from corrosion.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Embodiments herein may also be delivered as part of a service engagement with a client corporation, nonprofit organization, government entity, internal organizational structure, or the like. These embodiments may include configuring a computer system to perform some or all of the methods described herein, and deploying software, hardware, and web services that implement some or all of the methods described herein.

One skilled in the art will appreciate that many variations are possible within the scope of the present invention. Thus, while the present invention has been particularly shown and described with reference to the preferred embodiments thereof, it will be understood by those skilled in the art that these and other changes in form and detail may be made therein without departing from the spirit and scope of the present invention.

What is claimed is:

1. A method for detecting the presence of elemental sulfur in air, the method comprising the steps of:
    exposing a substrate to air from a surrounding environment, wherein the substrate includes a polymer-bound phosphine compound having a sulfur-getting functionality, wherein the substrate is mounted in a sample compartment;
    monitoring a fluorescence intensity of the substrate in real time;
    detecting a change in the fluorescence intensity of the substrate;
    determining whether the change in the fluorescence intensity of the substrate is above a predetermined threshold; and
    triggering an alarm if the change in the fluorescence intensity is above the predetermined threshold;
    wherein the step of exposing the substrate to air from the surrounding environment comprises the steps of
        sealing the sample compartment from the surrounding environment during measurements of the fluorescence intensity of the substrate, and
        opening the sample compartment to the surrounding environment during periods between the measurements.

2. The method as recited in claim 1, wherein the step of exposing the substrate to air from the surrounding environment includes the step of exposing the substrate to the air from a data center.

3. The method as recited in claim 1, wherein the polymer-bound phosphine compound is a substituted or unsubstituted phenylphosphine compound bonded directly to a polymer backbone.

4. The method as recited in claim 1, wherein the step of exposing the substrate to air from the surrounding environment further comprises the step of:
    drawing air from the surrounding environment into the sample compartment during the periods when the sample compartment is open.

5. A method for detecting the presence of elemental sulfur in air, the method comprising the steps of:
    providing a sulfur detection system comprising a spectrofluorometer, at least one processor, and at least one memory coupled to the at least one processor, wherein the at least one memory is encoded with instructions that when executed by the at least one processor cause the sulfur detection system to perform a detection process;
    performing the detection rocess using the sulfur detection system wherein the detection process comprises the steps of:
        exposing a substrate mounted in a sample compartment of the spectrofluorometer to air from a surrounding environment, wherein the substrate includes a polymer-bound phosphine compound having a sulfur-getting functionality, wherein the spectrofluorometer is operative to measure a fluorescence intensity of the substrate, and wherein the step of exposing the substrate mounted in the sample compartment of the spectrofluorometer to air from the surrounding environment comprises the steps of:

closing the sample compartment from the surrounding environment during measurements by the spectrofluorometer of the fluorescence intensity of the substrate, and opening the sample compartment to the surrounding environment during periods between measurements by the spectrofluorometer of the fluorescence intensity of the substrate;

monitoring the fluorescence intensity of the substrate in real time by repeatedly performing measurements of the fluorescence intensity of the substrate mounted in the sample compartment of the spectrofluorometer;

detecting a change in the fluorescence intensity of the substrate;

determining whether the change in the fluorescence intensity of the substrate is above a predetermined threshold; and triggering an alarm if the change in the fluorescence intensity is above the predetermined threshold.

6. The method as recited in claim 5, wherein the air from the surrounding environment includes air from a data center.

7. The method as recited in claim 5, wherein the polymer-bound phosphine compound is a substituted or unsubstituted phenylphosphine compound bonded directly to a polymer backbone.

8. The method as recited in claim 5, wherein the step of exposing the substrate mounted in the sample compartment of the spectrofluorometer to air from the surrounding environment further comprises the step of drawing air from the surrounding environment into the sample compartment during the periods when the sample compartment is open.

9. The method as recited in claim 5, wherein the step of opening the sample compartment to the surrounding environment during periods between measurements by the spectrofluorometer of the fluorescence intensity of the substrate includes opening at least one door to open the sample compartment to the surrounding environment during periods between measurements by the spectrofluorometer, and wherein the step of closing the sample compartment from the surrounding environment during measurements by the spectrofluorometer of the fluorescence intensity of the substrate includes closing the at least one door to close the sample compartment from the surrounding environment during measurements by the spectrofluorometer.

10. The method as recited in claim 9, wherein the at least one door each comprise a solenoid valve, wherein the step of opening the at least one door includes the step of activating the solenoid valve, and wherein the step of closing the at least one door includes the step of deactivating the solenoid valve.

11. The method as recited in claim 5, wherein the step of opening the sample compartment to the surrounding environment during periods between measurements by the spectrofluorometer of the fluorescence intensity of the substrate includes turning on a fan and opening an air intake door and an air exhaust door to draw air from the surrounding environment through the sample compartment during periods between measurements by the spectrofluorometer, and wherein the step of closing the sample compartment from the surrounding environment during measurements by the spectrofluorometer of the fluorescence intensity of the substrate includes turning off the fan and closing the air intake door and the air exhaust door to close the sample compartment from the surrounding environment during measurements by the spectrofluorometer.

12. The method as recited in claim 11, wherein the air intake door and the air exhaust door each comprise a solenoid valve, wherein the step of opening the air intake door and the air exhaust door includes the step of activating each solenoid valve, and wherein the step of closing the air intake door and the air exhaust door includes the step of deactivating each solenoid valve.

* * * * *